United States Patent [19]
Jensen

[11] Patent Number: 5,447,510
[45] Date of Patent: Sep. 5, 1995

[54] APPARATUS COMPRISING AN ULTRASONIC PROBE FOR REMOVING BIOLOGIC TISSUE

[75] Inventor: Jorgen Jensen, Hasle, Denmark
[73] Assignee: Baltic Technology ApS, Hasle, Denmark
[21] Appl. No.: 244,203
[22] PCT Filed: Jan. 21, 1993
[86] PCT No.: PCT/DK93/00020
§ 371 Date: Jun. 1, 1994
§ 102(e) Date: Jun. 1, 1994
[87] PCT Pub. No.: WO93/13715
PCT Pub. Date: Jul. 22, 1993

[30] Foreign Application Priority Data
Jan. 21, 1992 [DK] Denmark .................... 0074/92
[51] Int. Cl.6 ............................................. A61H 23/00
[52] U.S. Cl. .......................................... 606/1; 604/22; 607/97
[58] Field of Search ................. 606/1; 604/22; 607/97

[56] References Cited
U.S. PATENT DOCUMENTS

| | | |
|---|---|---|
| 4,886,060 | 12/1989 | Wiksell . |
| 4,974,581 | 12/1990 | Wiksell ............................ 604/22 X |
| 4,989,588 | 2/1991 | Kubota et al. .................... 604/22 X |
| 5,069,664 | 12/1991 | Guess et al. . |
| 5,112,300 | 5/1992 | Ureche ............................. 604/22 |
| 5,167,619 | 12/1992 | Wuchinich ....................... 604/22 |
| 5,242,385 | 9/1993 | Strukel ............................. 604/22 |
| 5,267,954 | 12/1993 | Nita ................................. 604/22 |

Primary Examiner—Peter A. Aschenbrenner
Attorney, Agent, or Firm—Kerkam, Stowell, Kondracki & Clarke

[57] ABSTRACT

Apparatus for ultrasonically removing biological tissue using an axially vibrating probe, and method of making same, including a housing having an outer portion forming a handle, wherein the housing has a sleeve therein supporting a piezoelectrical transducer with planar piezoelectrical elements arranged in parallel relation with an axis of the probe. An armature is provided which operatively connects the probe with the piezoelectrical elements, wherein the piezoelectrical elements are arranged between outwardly facing sides of the armature and inwardly facing sides of filling bodies inserted in the sleeve, respectively. An intermediate layer of electrically conductive foil is located between the piezoelectrical elements and the outwardly facing sides of the armature and the inwardly facing sides of the filling bodies, respectively. The piezoelectrical elements have a crystalline structure which, when an electric voltage is applied between the outwardly facing sides of the armature and the inwardly facing sides of the filling bodies, the piezoelectrical elements are displaced in an axial direction relative to the probe. The sleeve is constructed such that the sleeve tightly encircles the filling bodies to provide a frictional engagement between the piezoelectrical elements and the filling bodies and the armature, respectively.

13 Claims, 2 Drawing Sheets

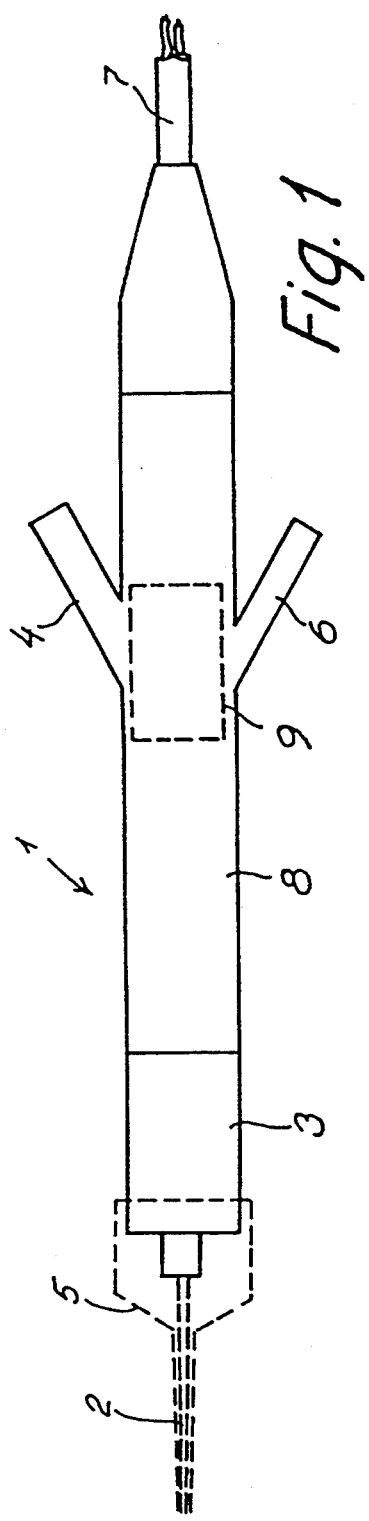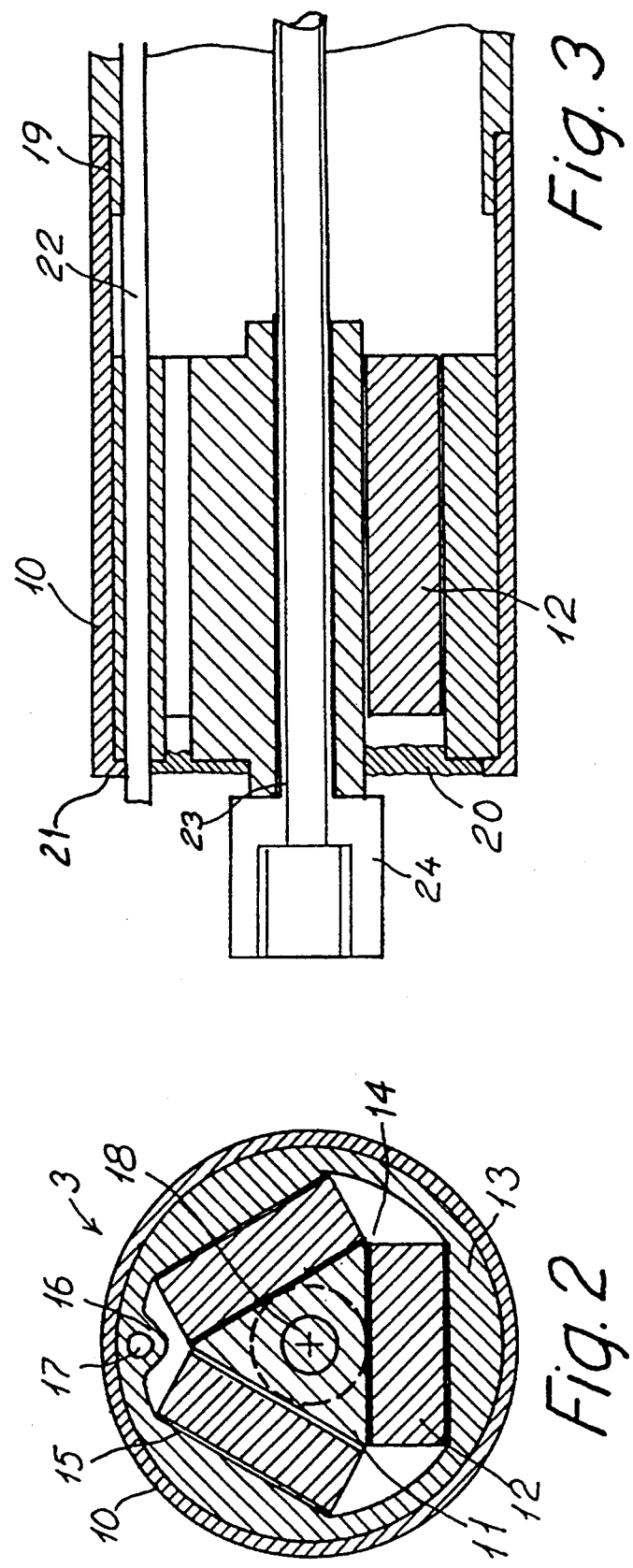

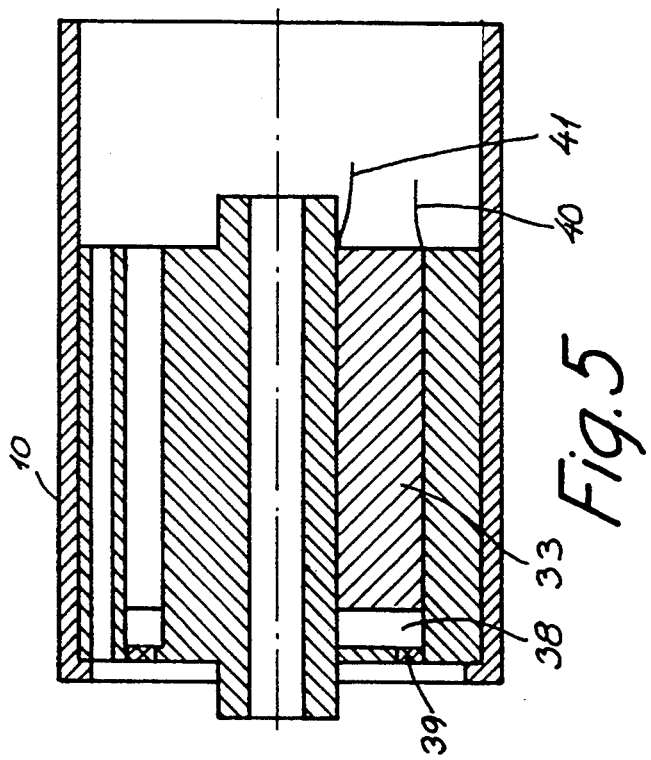
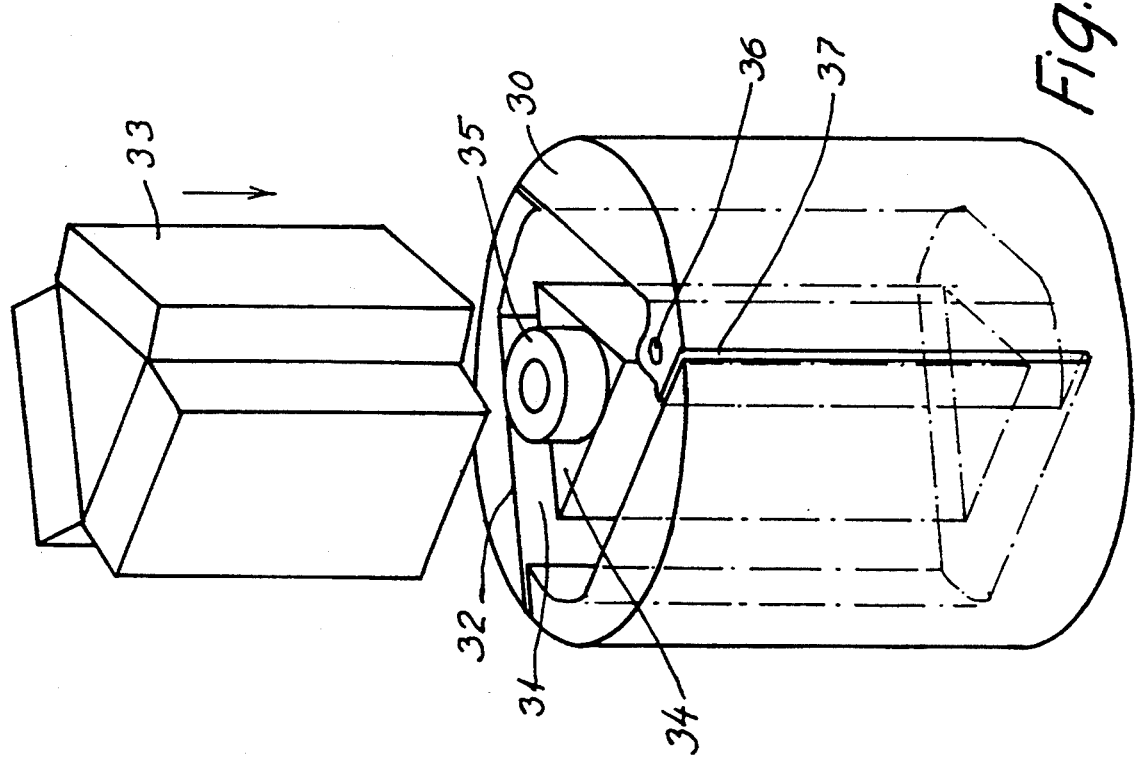
Fig. 5
Fig. 4

APPARATUS COMPRISING AN ULTRASONIC PROBE FOR REMOVING BIOLOGIC TISSUE

FIELD OF THE INVENTION

The present invention relates to an apparatus comprising an ultrasonic probe for removing biologic tissue, said apparatus being of the type described in the preamble of claim 1. The invention also relates to a method for producing a preferred embodiment of the apparatus.

BACKGROUND OF THE INVENTION

In apparatuses of this kind the probe, the armature, to which is it fastened, and one or more piezoelectric crystals form an oscillating system with a resonance frequency corresponding to the frequency, at which work is desired to be carried out. In the known apparatuses the piezoelectric crystals are shaped like discs placed perpendicular to the axis of the probe and fixed with a mounting of the crystal in such a way that an electric activation brings about a mechanical change of the crystal in the axial direction of the probe. To attain a sufficient mechanical effect the crystal should have a certain area, which makes it necessary that the housing in order to hold the crystals should have a diameter of 20 nm or more. The comparatively big diameter of the cross-section of the housing makes the apparatus awkward to hold, which makes it in particular tiring to work with when very precise movements are to be carried out with the point of the probe, which is of particular importance when such apparatus are used for surgical interventions in human eyes, in which connection work is carried out with the apparatus under microscope. The comparatively big dimensions of the crystal or the crystals also contribute to making it difficult to attain very high resonancy frequencies on account of the comparatively big masses of armature and probe. It is thus difficult to attain resonance frequencies in the area of 50 to 100 kHz.

OBJECT AND SUMMARY OF THE INVENTION

The object of the invention is to provide an apparatus of the above-mentioned type, but in connection with which it is possible partly to reduce the diameter of the housing, partly to attain resonancy frequencies in the area between 50 and 100 kHz without any specific measures.

This object is met by the apparatus according to the invention and mentioned by way of introduction, said apparatus being characteristic in the subject matter of the characterizing clause of claim 1.

In the apparatus according to the invention, the armature, on which the probe is fastened, is most compact and consequently of a limited mass, which contributes to increasing the resonance frequency. The armature is directly suspended in the two, three or four piezoelectric crystals acting in shear mode. These crystals form a comparatively rigid suspension, which also contributes to giving the system comprising armature and probe a high resonance frequency. As the piezoelements are placed in the longitudinal direction of the probe, they can be given a comparatively big area without affecting the diameter of the apparatus. The diameter of the apparatus may therefore be small and contained in a very slim housing, an instrument being thus provided which is easy to work with. The design is in particular favourable in connection with apparatuses aiming at an axial vibration of the probe, but is in special embodiments also applicable in apparatuses, where the ultrasonic vibration produces a vibration perpendicular to the axis of the probe. However, the latter embodiment requires that only two piezo elements be used, and that they are oriented in such a way the they act in shear mode perpendicular to the axis of the probe, but still, however, in such a way that the plane of the piezo elements is running parallel to the axis of the probe. Whereas the apparatus with the axial vibration is in particular suited for eye operations, the other apparatus vibrating perpendicular to the longitudinal direction of the probe will be suited for cleaning operations, for instance removal of plaque and tartars from teeth.

According to a preferred embodiment of the apparatus the armature and preferably also the segments placed between the piezo bodies and the sleeve are made from anodized aluminum. The anodizing forms an effective electric insulation, which is solely able to insulate for the alternating voltage necessary for the activation of the piezo elements and which should be supplied to conductive intermediate layers placed between the crystals and the armature.

Alternatively, the armature and possibly the segments may consist of a ceramics based on an aluminium oxide. The ceramic material has both strength and insulating properties, which are well suited for the purpose, and the parts can be manufactured with the required exactness by a comparatively simple moulding process. Also the ceramic material has a comparatively low specific gravity, which in connection with the armature designed with small dimensions contributes to the attainment of high resonance frequencies in the vibration system suspended by means of the piezo bodies, should this be required.

The invention also relates to a method for the manufacture of the apparatus. The method according to the invention is characterized by the subject matter of claim 5.

By the method according to the invention a groove is made from one end face in a cylindric body, said groove having a depth sufficient for holding the piezoelectric crystals. Before these are inserted with the necessary intermediate layers of electrically conductive material, the cylindric body is anodized, the body becoming generally coated with a layer of electrically insulating oxides. The plane-parallel faces of the grooves are in particular provided with this insulating coating. After insertion, the crystals are fixed between the plane-parallel faces by eclipsing on the encircling sleeve, and after the last shortening of the body, by which that part of the body forming the bottom of the groove is removed, the piezoelectric crystals become the only connection between the encircling sleeve and the armature, which resulted as the remaining part by the manufacture of the peripheral groove.

According to the method it is preferred to mount the piezoelectric elements at a distance from the bottom of the groove when mounting the encircling sleeve. By this arrangement it is possible by the shortening, in connection with which the anodizing is broken, to attain an ample distance between these surfaces and the piezo elements in order not to break the insulation between the piezo elements and the armature on one hand and the sleeve on the other.

To facilitate the mounting of the encircling sleeve for tightening the plane-parallel grooves around the piezo elements it is preferred according to the invention to provide the circumferential groove with widenings cutting through the side walls between the plane-parallel sections. These widenings may be quite narrow, wall sections being thus left between the sections forming the plane-parallel grooves, said wall sections having sufficient material for holding ducts for transportation of liquid past the armature.

According to the invention the groove is made by spark machining, this way of manufacture providing the necessary liberty as to the working out of the circumferential groove and in particular the liberty to let the remaining wall sections have thickenings and the like for the passing of liquid ducts.

BRIEF DESCRIPTION OF THE DRAWINGS

The invention will be described in detail in the following with reference to the drawings, in which FIG. 1 is a lateral view of the apparatus according to the invention, the probe being indicated with dotted lines, FIG. 2 is a sectional view through the front part of the apparatus along the line II—II of FIG. 3, FIG. 3 is an axial view through the front part of the apparatus with the armature and its support, FIG. 4 is a diagonal view of a production stage of the apparatus, before the mounting of the piezoelectric crystals in the grooves in the aluminum body, and FIG. 5 is a longitudinal section through the armature and its support, before the armature is separated from the parts of the aluminum body connected with the sleeve.

DESCRIPTION OF THE PREFERRED EMBODIMENTS

The apparatus 1 shown from the side in FIG. 1 is preferably applicable for removal of biologic tissue, for instance in connection with eye operations. At such operations the lens, which may be blurred on account of for instance cataract, is removed by means of a tubular vibrating probe 2 indicated in the figure by dotted lines. The probe 2 is by means of an ultrasonic vibrator placed in the front part 3 of the apparatus made to perform axial vibrations in the frequency range 25 to 100 kHz. The apparatus is on its housing provided with an inlet 4, through which a biologic saline solution may be conveyed to the front part of the apparatus, on which a pointed jacket is mounted, into which the duct connected to the inlet 4 discharges. By the vibration the probe 2 comminutes the biologic tissue and brings it in suspension in the saline solution, after which it through the hollow probe may be sucked away through the discharge pipe 6. The apparatus is at its rear end provided with an electric connection 7 to a generator for high-frequency electric oscillating impulses, which are adjusted to the resonance frequency of the vibrator in such a way that the system consisting of the armature of the vibrator and the probe is made to vibrate at the adjusted frequency. The housing of the apparatus forms a handle for guiding the probe, and it is therefore shaped as a slim tube 8, which is moreover at the inside charged with a lead in a suitable place, the apparatus fitting conveniently in the hand and being guidable nearly as a pencil.

The characteristic feature of the apparatus according to the invention is the front part 3 containing the vibrator, which is able to transfer a considerable energy to the armature of the vibrator, as well as distinguishes itself by being most compact. The compact design of the vibrator is the reason why the apparatus may be manufactured as a slim instrument with a diameter of approx. 10 mm, which makes the apparatus easy to handle. The design of the vibrator can be seen from FIGS. 2 and 3, which show a cross section and an axial section, respectively, through the apparatus according to the invention.

The vibrator 3, which in FIG. 2 is shown in cross section, comprises a tubular sleeve 10, which holds the vibrator itself fixed. The vibrator is provided with an armature 11, which in the shown embodiment has a triangular cross-section, and against the side faces of which three piezoelectric elements 12 rest. Between the piezoelectric elements 12 and the sleeve three filling bodies 13 are inserted. The piezoelectric elements 12 have such a crystalline structure that they, when an electric voltage is applied between the two faces, with which they rest against the armature 11 and the filling bodies 13, bring about a displacement in the longitudinal direction of the armature. Between the armature and the individual piezo elements partly an insulating layer is inserted, partly an electrically conductive plate 14. The insulation is preferably established thereby that the armature, which is made from aluminum of a suitably hard and strong alloy, is provided with an anodization, while the conductive plate 14 just is a metal foil, for instance a stainless steel foil. Between the piezoelectric elements and the filling bodies an electrically conductive plate 15 and an insulating layer have been inserted in a similar way. The filling bodies are like the armature made from anodized aluminum, the anodizing forming the insulating layer. In the area between the individual piezoelectric elements the filling bodies may be provided with flanges 16, which may contain a widening with a channel 17. The channel may serve for the conveyance of liquid around the probe fastened to the armature. Furthermore, the armature is provided with an axial bore, which both serves for the screwing in of the probe and further may serve as a return duct for the liquid sucked away through the hollow probe. FIG. 3 is a longitudinal section through the vibrator according to FIG. 2. The sleeve 10 is adapted for being fastened to the housing 1 and has therefore been extended so much that a free end may be fixed in a recess 19 on the front end of the housing. The tubular sleeve 10 has a collar 21 in front, which serves as a stop at the insertion of the components of the vibrator during the production, and which facilitates the mounting of the jacket. The collar 21 furthermore shields an resilient sealing 20, which prevents liquid supplied around the probe from short-circuiting between the conductive plates on the piezoelectric elements 12. Through the duct 17 a tube 22 is passed, said tube discharging in front of the collar 21, and which is used for conveying a saline solution to the area around the probe. The probe is inserted in the central boring 18 in the armature and is fastened against the front side of the armature, on which a tubular connecting piece 23 may be placed. The tubular connecting piece 23 gives together with a sleeve 24 for the actual fastening of the probe a possibility for tuning the resonance frequency of the system consisting of armature 11, probe 2 and sleeve 24 in such a way that the frequency corresponds to the vibration frequency, at which you want to work, for instance 60 kHz.

The manufacture of the vibrator according to the invention may advantageously take place by the following method:

In a cylindrical body 30 of aluminum a circumferential groove 31 is made by spark machining with a shape essentially corresponding to a triangle. The groove is made with a depth somewhat higher than the height of the piezoelectric elements, with which the vibrator is to be equipped. The groove 31 is made with three sections having opposite plane-parallel walls 32 with a mutual distance just big enough for the insertion of a piezoelectric body 33 in the groove with a metal foil on either side. When making the groove a triangular prism 34 remains in the middle, said prism becoming, when the vibrator is finished, its armature. It is advantageous that the end faces of the cylindric body are turned before the making of the circumferential groove, the protruding cylndrical sleeves being producible while the body possesses the required rigidity. In the areas between the sections provided with the plane-parallel walls comparatively thin-walled sections of the body are left, but there is, however, room for widenings, through which channels 36 may be made for the taking up of tubes for the conveyance of liquid or wires. The thin-walled sections are cut through with a narrow cut 37 making it possible to press together the three thereby separated parts of the body 30 by mounting a tight sleeve pressing the plane-parallel faces together against the sides of the piezoelectric elements 33 inserted in the grooves. Before the insertion of these elements, the aluminum body is subjected to anodizing, whereby a layer of aluminum oxides are formed on the surface, which gives an effective electric insulation. A particular property of the anodizing is that the layer in a simple way acquires a homogeneous thickness, whereby the tolerances of the groove sections, in which the piezoelectric bodies are inserted, do not change after the mechanical machining. FIG. 5 shows the vibrator after the mounting of the sleeve in an axial view. It will be seen that the piezoelectric bodies do not extend completely to the bottom of the groove, but that an interspace 38 is present at the bottom of the groove. By the mounting of the sleeve the armature 34 of the vibrator has been fastened between the three piezoelectric bodies 33, and the vibrator forms a whole. To make the armature capable of making a high-frequency oscillation in axial direction what remains is just to stake out a groove in the end wall for removal of the material 39, which is cross-hatched in FIG. 5. Between the anchor and the sleeve, which is preferably equipped with a collar, a resilient mass, for instance silicone rubber, is placed. The electrically conductive plates on the sides of the piezoelectric bodies are provided with protruding flanges 40,41 serving as terminals for the alternating current to run the vibrator. The vibrator is now essentially ready for being mounted in the tube 8.

The vibrator described above is provided with three piezoelectric elements, which in most cases must be regarded as the most advantageous. However, the invention is not limited to vibrators with three piezoelectric crystals. In a completely analogous way vibrators with more than three bodies, for instance four, may be produced, though an increase of the number makes greater requirements to the production tolerances when making the circumferential groove. Correspondingly, vibrators may be produced within the scope of the invention with only two piezo elements. The armature will then not get the shape of a regular prism, but the shape of a body symmetrical about a plane around the axis of the probe with two identical side faces. The identical side faces will be connected with two other side faces, which do not have to be plane, but which may be designed in such a way that suitable openings through the vibrator are provided for the conveyance of the saline solution. According to the invention an apparatus with only two piezo elements also be designed in such a way that the vibration only takes place in a direction perpendicular to the axis of the probe. In relation to the normal design, in which the shear mode direction of the piezo elements runs parallel with the probe, the elements are turned 90° in their own plane. Vibrators acting perpendicularly to the direction of the probe require a particularly careful construction of the probe, as it has to be designed in such a way that the induced vibration is transmitted to the active point of the probe.

As described above it is a prerequisite for the above preferred method for producing the vibrator that the armature is made from aluminum. Other metallic materials may be used, but the advantage of being able to provide the insulating surface layer by anodizing is thereby lost. However, it is not a prerequisite for the apparatus according to the invention that the armature and the filling bodies are made of metal. In an alternative embodiment according to the invention the armature and preferably also the filling bodies are made from ceramics on basis of aluminum oxide. This material will in the same way as the anodized aluminum possess electrically insulating properties, whereby other measures for insulating against the alternating current, which drives the vibrator, are made superfluous.

I claim:

1. An apparatus for ultrasonically removing biological tissue using an axially vibrating probe, said apparatus comprising a housing having an outer portion forming a handle, said housing having a sleeve therein supporting a piezoelectrical transducer comprising planar piezoelectrical elements arranged in parallel relation with an axis of the probe, and an armature which operatively connects said probe with said piezoelectrical elements, wherein said piezoelectrical elements are arranged between outwardly facing sides of the armature and inwardly facing sides of filling bodies inserted in said sleeve, respectively, wherein an intermediate layer of electrically conductive foil is located between said piezoelectrical elements and said outwardly facing sides of said armature and said inwardly facing sides of said filling bodies, respectively, said piezoelectrical elements having a crystalline structure which, when an electric voltage is applied between said outwardly facing sides of said armature and said inwardly facing sides of said filling bodies, causes said piezoelectrical elements to be displaced in an axial direction relative to the probe, said sleeve being constructed such that said sleeve tightly encircles said filling bodies to provide a frictional engagement between said piezoelectrical elements and said filling bodies and said armature, respectively.

2. Apparatus according to claim 1, wherein said armature and said filling bodies are made from anodized aluminum.

3. Apparatus according to claim 1, wherein said armature and said filling bodies are made from aluminum oxide.

4. Apparatus according to claim 2, wherein said armature and said filling bodies are made from aluminum oxide.

5. Apparatus according to claim 1, wherein said armature has a triangular shape.

6. Apparatus according to claim 1, wherein said armature is shaped as a four-sided prism.

7. A method of manufacturing an apparatus for ultrasonically removing biological tissue having an axially vibrating probe, comprising the steps of providing an aluminum body member having a circular cross-section, making a circumferential groove in said body member from one end thereof in a manner which defines a plurality of parallel pairs of radially inwardly and radially outwardly facing planer surfaces within said body member, anodizing said body member, inserting a plurality of piezoelectrical elements in said body member between said parallel pairs of radially inwardly and radially outwardly facing planar surfaces, respectively, wherein each of said piezoelectrical elements includes an electrical conducting sheet on a radially inwardly and radially outwardly facing surface thereof, and mounting a tight-fitting sleeve member around said body member in a manner which causes said piezoelectrical elements to be frictionally engaged between said parallel pairs of radially inwardly and radially outwardly facing surfaces in said body member, respectively.

8. A method according to claim 7, further including forming said circumferential groove such that said piezoelectrical elements are spaced from a bottom thereof when inserted in said body member.

9. A method according to claim 7, further including making a plurality of longitudinal cuts in said body member which extend from an outer surface of said body member into said circumferential groove, wherein said cuts meet said circumferential groove at a location adjacent to a space defined between said parallel pairs of radially inwardly and radially outwardly facing planar surfaces, respectively, said cuts being made prior to inserting said piezoelectrical elements in said body member.

10. A method according to claim 8, further including making a plurality of longitudinal cuts in said body member which extend from an outer surface of said body member into said circumferential groove, wherein said cuts meet said circumferential groove at a location adjacent to a space defined between said parallel pairs of radially inwardly and radially outwardly facing planar surfaces, respectively, said cuts being made prior to inserting said piezoelectrical elements in said body member.

11. A method according to claim 7, further including using a spark machining device to make said circumferential groove.

12. A method according to claim 8, further including using a spark machining device to make said circumferential groove.

13. A method according to claim 9, further including using a spark machining device to make said circumferential groove.

* * * * *